(12) United States Patent
Bischoff

(10) Patent No.: US 9,585,833 B2
(45) Date of Patent: Mar. 7, 2017

(54) ELEMENT FOR IMPLANTATION WITH MEDICAL DEVICE

(75) Inventor: Thomas C. Bischoff, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 902 days.

(21) Appl. No.: 13/310,860

(22) Filed: Dec. 5, 2011

(65) Prior Publication Data

US 2012/0078165 A1     Mar. 29, 2012

Related U.S. Application Data

(62) Division of application No. 12/413,714, filed on Mar. 30, 2009, now Pat. No. 8,092,443.

(51) Int. Cl.
    *A61K 9/00*        (2006.01)
    *A61M 31/00*     (2006.01)
    *A61M 25/00*     (2006.01)
    *A61M 37/00*     (2006.01)

(52) U.S. Cl.
CPC ......... *A61K 9/0024* (2013.01); *A61M 31/002* (2013.01); *A61M 37/0069* (2013.01); *A61M 2025/0056* (2013.01); *A61M 2025/0057* (2013.01)

(58) Field of Classification Search
CPC .. A61M 2025/0056; A61M 2025/0057; A61M 31/002; A61K 9/0024
USPC ................... 604/500, 502, 506, 890.1, 891.1
See application file for complete search history.

(56) References Cited

U.S. PATENT DOCUMENTS

| | | | |
|---|---|---|---|
| 5,217,493 A | 6/1993 | Raad | |
| H001465 H | 7/1995 | Stokes | |
| 5,902,283 A | 5/1999 | Darouiche | |
| 6,162,487 A | 12/2000 | Darouiche | |
| 6,228,052 B1 | 5/2001 | Pohndorf | |
| 6,847,849 B2 | 1/2005 | Mamo | |
| 6,887,270 B2 | 5/2005 | Miller | |
| 6,968,234 B2 * | 11/2005 | Stokes | 607/36 |
| 7,427,280 B2 * | 9/2008 | Gerber | 604/502 |
| 7,596,408 B2 | 9/2009 | Singhal | |

(Continued)

FOREIGN PATENT DOCUMENTS

| | | |
|---|---|---|
| EP | 640661 | 3/1995 |
| WO | WO 96/39215 | 12/1996 |
| WO | WO 2004/084955 | 10/2004 |

OTHER PUBLICATIONS

PCT Search Report and Written Opinion dated Jun. 18, 2010.

*Primary Examiner* — Kevin C Sirmons
*Assistant Examiner* — Benjamin Koo
(74) *Attorney, Agent, or Firm* — Mueting, Raasch & Gebhardt, P.A.

(57) ABSTRACT

A therapeutic agent eluting element includes an elongate body member and one or more therapeutic agents elutable from the body member. The elongate body member is configured to be implanted subcutaneously along side of a therapy delivery element. The elongate body member may be formed from a polymeric material, and the agent eluting element may consist essentially of the body member and the one or more therapeutic agents. The therapeutic agent eluting element may be a part of a system or kit that includes a therapy delivery element and a tunneling tool, such as a dilator, sheath, catheter passer, or the like.

10 Claims, 10 Drawing Sheets

(56) References Cited

U.S. PATENT DOCUMENTS

| | | |
|---|---|---|
| 8,092,443 B2 * | 1/2012 | Bischoff ................ 604/500 |
| 8,267,905 B2 * | 9/2012 | Lobl et al. ............ 604/288.01 |
| 2002/0111603 A1 | 8/2002 | Cheikh |
| 2004/0073197 A1 | 4/2004 | Kim |
| 2004/0186528 A1 | 9/2004 | Ries |
| 2005/0079199 A1 | 4/2005 | Heruth |
| 2005/0245846 A1 * | 11/2005 | Casey ............... A61M 25/0127 |
| | | 600/585 |
| 2005/0267543 A1 | 12/2005 | Heruth |
| 2006/0009806 A1 | 1/2006 | Heruth |
| 2006/0039946 A1 | 2/2006 | Heruth |
| 2006/0051392 A1 | 3/2006 | Heruth |
| 2006/0051393 A1 | 3/2006 | Heruth |
| 2006/0074388 A1 | 4/2006 | Dextradeaur |
| 2007/0275035 A1 | 11/2007 | Herman |
| 2008/0125728 A1 | 5/2008 | Bischoff |
| 2008/0128315 A1 | 6/2008 | Buevich |
| 2008/0132922 A1 | 6/2008 | Buevich |
| 2008/0241212 A1 | 10/2008 | Moses |
| 2008/0260796 A1 | 10/2008 | Bischoff |
| 2008/0269716 A1 * | 10/2008 | Bonde et al. ............ 604/506 |
| 2009/0198197 A1 | 8/2009 | Bischoff |

* cited by examiner

ELEMENT FOR IMPLANTATION WITH MEDICAL DEVICE

RELATED APPLICATION

This application is a divisional of U.S. application Ser. No. 12/413,714 filed Mar. 30, 2009 now U.S. Pat. No. 8,092,443, and titled "ELEMENT FOR IMPLANTATION WITH MEDICAL DEVICE". The entire disclosure of this application is incorporated herein by reference.

FIELD

This disclosure relates, inter alia, to implantable medical devices. More particularly, it relates to systems, methods and devices for delivering a therapeutic substance from a cord or tube implanted with a lead or catheter.

BACKGROUND

Implantation of medical devices, such as pacemakers, neurostimulators, implanted drug pumps, leads, catheters, etc. has been associated with adverse consequences, such as formation of scar tissue surrounding the implant and infection due to bacteria introduced during implantation. Attempts to prevent or control such adverse reactions have included administration of drugs, completely separate from the intended primary therapy of the implanted medical device. In some cases, systemically administered drugs, e.g. orally, intravenously, or intramuscularly administered drugs, have proven effective in treating complications due to medical device implantation. In other cases, systemic delivery has been ineffective due to, e.g., pharmacokinetic or pharmacodynamic characteristics of the drug, the location of the implanted device, or side effects of the drug. To increase effectiveness in these situations, some implanted devices have been modified to elute the drug into the surrounding tissues.

One common way of providing local drug elution is to dispose a polymer layer on the implantable medical device and embed the drug into the polymer during manufacturing. When hydrated after implant, the drug diffuses out of the polymer into surrounding tissue. Various methods of impregnating polymers with drugs have been used, including mixing the drug into the melted polymer prior to processing (e.g. molding or extrusion), and diffusing the drug into a finished polymer component using chemicals to swell the polymer for rapid loading. In some cases, the implantable medical device (IMD) is made from a polymer that is compatible with the drug, and the drug can be loaded directly into the device. However, incorporation of a therapeutic agent into or onto polymeric material may compromise the structural integrity of the material.

Structural integrity of catheters and leads, especially those intended to be chronically or permanently implanted, are important. Such catheters and leads, which are typically made using standard polymeric tubing, such as silicone or polyurethane, are tunneled subcutaneously from a pocket into which an active device, such as a drug pump or neurostimulator, is implanted to the therapy delivery site. For neurological systems, the therapy delivery site is typically the spinal intrathecal space, the spinal epidural space, the ventricles of the brain, or brain parenchyma. For cardiac systems, the therapy delivery site is the heart. Because, the catheters and leads are implanted long term and may be tunneled through a subcutaneous path, it may not be desirable to compromise the structural integrity of such devices.

In addition, the active agent disposed on or in the structural body of a catheter or lead can diffuse inward to the catheter drug path or the lead conductors as readily as it diffuses outward to the subcutaneous tissue. Diffusion of the elutable agent into the drug flow path of a catheter may result in undesired interaction of the drug delivered by the catheter and the elutable agent or may cause the elutable agent to be delivered to an area of the body on which its effects may be undersiable. For example, the elutable agent is intended to be delivered to subcutaneous tissue, and may have deleterious effects at the site of therapy delivery, e.g. the central nervous system (CNS). For stimulation leads, the active agent could cause corrosion of the metallic conductors or electrodes. For both types of devices, adding the active agent results in an extra manufacturing process that complicates manufacturing. In addition, the shelf life of a catheter or lead having an associated therapeutic agent may be considerably less than the shelf life of a catheter or lead without an associated therapeutic agent.

SUMMARY

The present disclosure describes, inter alia, an accessory implantable device that includes an elutable therapeutic agent. The therapeutic agent eluting element may be in any suitable form, such as a rod or tube, and may be implanted along side of a therapy delivery element, such as a lead or catheter, to treat or prevent diseases or symptoms associated with implanting a therapy delivery element. For example, the therapeutic agent eluting element may elute one or more agent to treat or prevent scar formation, infection or pain.

In an embodiment, a therapeutic agent eluting element include an elongate body member and one or more therapeutic agents elutable from the body member. The elongate body member is configured to be implanted subcutaneously along side of a therapy delivery element. The body member may be formed from a polymeric material, and the agent eluting element may consist essentially of the body member and the one or more therapeutic agents. The therapeutic agent eluting element may be a part of a system or kit that includes a therapy delivery element and a tunneling tool, such as a dilator, sheath, catheter passer, or the like.

In an embodiment, a method for implanting a therapeutic agent eluting element along side of an implantable therapy delivery element includes (i) tunneling a subcutaneous path in a patient for the implantable therapy delivery element; (ii) moving an end of the therapy delivery element through the tunneled path; and (iii) moving an end of a therapeutic agent eluting element through the tunneled path. The therapeutic agent is thus implanted along side of the therapy delivery element in the subcutaneous tissue to allow the therapeutic agent to elute into tissue surrounding the therapy delivery element to treat or prevent diseases or symptoms associated with implanting therapy delivery elements.

By providing accessory therapeutic agent-containing devices, the accessory device can be sterilized separately from the therapy delivery element, which may be helpful in situations where the therapeutic agent is not compatible with a sterilization process to which the therapy delivery element may be subjected. In addition, by incorporating the therapeutic agent into the accessory device, rather than the therapy deliver element, the therapeutic agent is less likely to compromise the structural integrity or adversely affect desired properties of the therapy delivery agent. Further, the accessory device allows a health care provider to make a determination as to whether to include the therapeutic agent-containing device in the implant procedure. Moreover, an accessory device may be packaged separately from the therapy delivery element, so the time the therapeutic agent-containing accessory device sits on the shelf may be kept to a minimum. These and other advantages will be readily understood from the following detailed descriptions when read in conjunction with the accompanying drawings.

Figure 1:
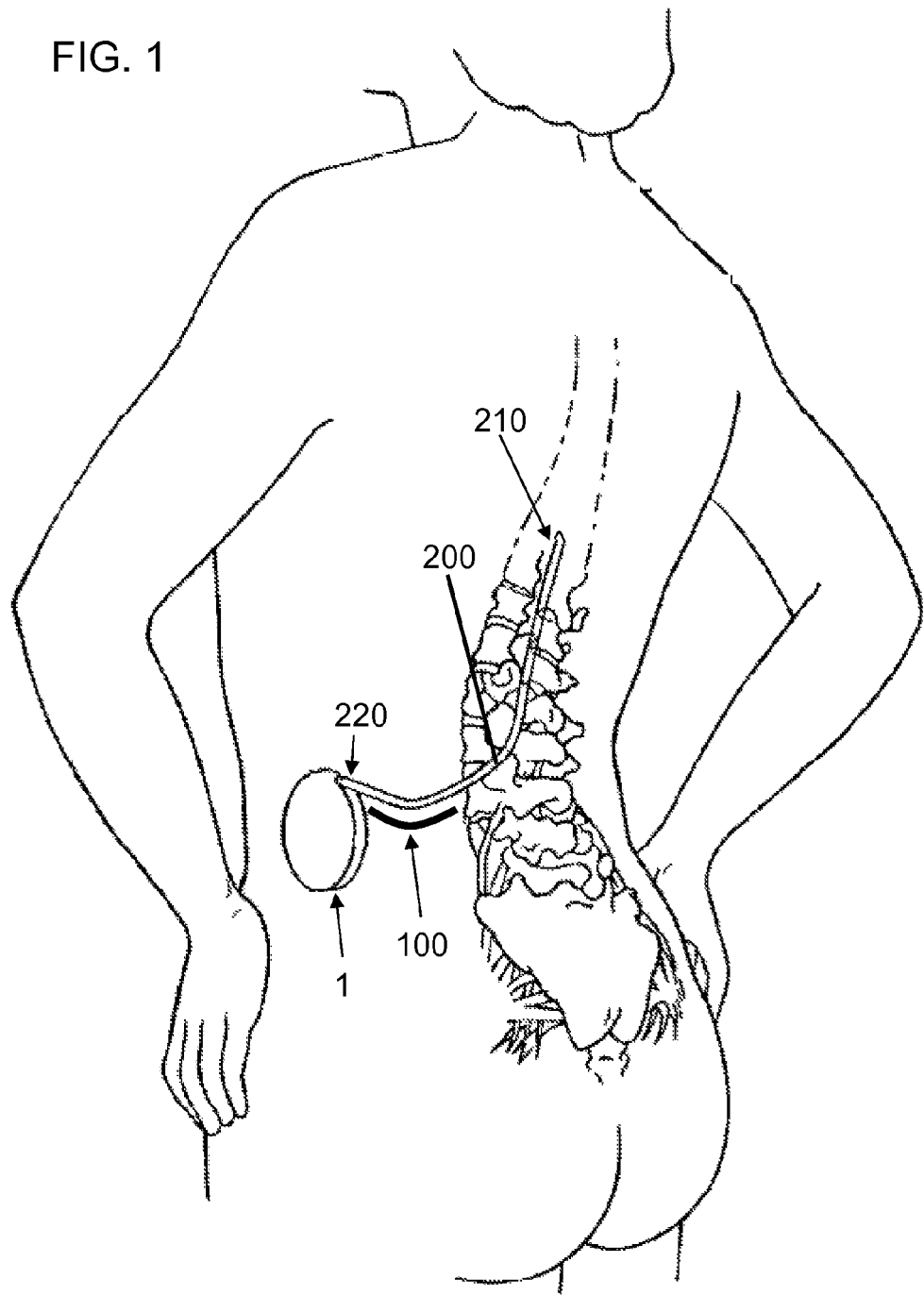
FIG. 1 is a schematic side view of an environment of a medical system implanted in a patient.

The drawings are not necessarily to scale. Like numbers used in the figures refer to like components, steps, etc. However, it will be understood that the use of a number to refer to a component, step, etc. in a given figure is not intended to limit the component, step, etc. in another figure labeled with the same number. In addition, the use of different numbers to refer to components, steps, etc. is not intended to indicate that the different numbered components, steps, etc. cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein, an "effective amount" of an anti-infective agent is an amount that prevents, reduces the severity of, or delays an infection.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "along side of", as it relates to an agent eluting element implanted relative to a therapy delivery element, means that at least a portion of the agent eluting element is implanted in proximity to the therapy delivery element along at least a portion of the length of the therapy delivery element. An agent eluting element implanted along side of a therapy delivery element may or may not run generally parallel to the therapy delivery element. In some embodiments, all, substantially all, or a substantial portion of the agent eluting element runs parallel to the therapy delivery element. For example, more than 70%, more than 80%, more than 90% or more than 95% of the length of the agent eluting element runs along side of the length of the therapy delivery element in generally the same direction of the therapy delivery element. It will be understood that, if the agent eluting element may be wrapped around or coiled around the therapy delivery element, the agent eluting element will be considered to run generally parallel to the therapy delivery element in wrapped or coiled region.

The present disclosure describes, inter alia, therapeutic agent eluting elements that may be implanted subcutaneously along side of a therapy delivery device, such as a lead or catheter. The therapeutic agent eluting element has an elongate body capable of releasing therapeutic agent in the subcutaneous tissue in which the therapy delivery element is implanted. By releasing the therapeutic agent in tissue in which the therapy delivery element is implanted, diseases associated with subcutaneous implantation of therapy delivery elements, such as infection, scarring, and pain can be mitigated. By incorporating the therapeutic agent in a separate element, the structural integrity of a therapy delivery device may be maintained and potentially undesirable interactions between the therapeutic agents and drugs that may delivered by the therapy delivery agent may be prevented. Because the therapeutic agent eluting element is separate from the therapy delivery element, the therapeutic agent eluting element may be subjected to a different sterilization process from the delivery element, which may be helpful in situations where the therapeutic agent is not compatible with the sterilization process of the therapy delivery element. Further advantages of having the therapeutic agent eluting element separate from the therapy delivery element until implantation, or just prior to implantation, include (i) the ability to package the agent eluting element and the delivery element separately so that the time agent eluting element remains on the shelf can be reduced, and (ii) allowing a physician or healthcare provider to make a determination as to whether to include the agent eluting element in the implant procedure or make a determination as to which therapeutic agent should be used with a particular implant procedure. These and other advantages will be readily understood from the following detailed descriptions when read in conjunction with the accompanying drawings.

Referring to FIG. 1, a general representative environment for an implanted active medical device 1, therapy delivery element 200 and therapeutic agent eluting element 100 are shown. Active medical device 1, such as a pacemaker, defibrillator, monitoring device, infusion device, neurostimulator, gastric stimulator, cochlar device, or the like, is implanted in a patient, for example in an abdominal region, in a subcutaneous "pocket". A distal portion 210 of therapy delivery element 200 is positioned in the patient at a location where therapy is desired to be delivered. In the embodiment depicted, the distal portion 210 of therapy delivery element 200 is positioned within or along a spinal canal or cord of a patient. However, it will be understood that distal portion 210 of therapy delivery element 200 may be placed in any desired location to achieve its intended purpose, such as a diagnostic, monitoring, or therapeutic purpose. Often, the distal portion 210 of the therapy delivery element 200 is positioned and anchored to inhibit movement of the distal therapy delivery region 210 as the proximal end 220 is tunneled subcutaneously to the "pocket" where the proximal end 220 of therapy delivery element 200 may be operably coupled to active medical device 1. In the depicted embodiment, a therapeutic agent eluting element 100 is implanted along side of the therapy delivery element 200 along the length that the therapy delivery element 200 is tunneled subcutaneously.

Therapy delivery element 200 may be a catheter, a lead or lead extension, or the like. In numerous embodiments, therapy delivery element 200 is an elongate element that can deliver therapy, withdraw fluid, sense a parameter, or diagnose a condition. Catheters are typically flexible tubes with a lumen running from the proximal end of the catheter to one or more delivery regions that are typically located at the distal portion of catheter. A proximal end of a catheter may be coupled to an implantable infusion device such that fluid may be delivered from the infusion device via the lumen of the catheter to a target location of a patient via one or more delivery regions of the catheter.

Leads typically include one or more electrical contacts on a proximal end portion and one or more electrodes on a distal end portion. The contacts and electrodes are electrically coupled via insulated wires running through the lead. The contacts may be electrically coupled with an implantable electrical signal generator, and signals generated by the generator may be carried along the lead and delivered to the patient via the electrodes. A lead may be connected to a signal generator medical device through a lead extension. An extension typically includes one or more contacts at the proximal and distal end portions that are electrically coupled through wires running through extension. Of course it will be understood that with some systems a lead may be directly connected to electrical signal generator without use of a lead extension. As used hereinafter, "leads" and "lead extensions" are used interchangeably, unless content clearly dictates otherwise.

While the active implantable medical device 1 depicted in FIG. 1 is shown implanted in an abdominal region, it will be understood that the device 1 may be implanted in any suitable location of a patient, such as in a pectoral region, behind a patient's ear, in a patient's buttocks or skull, or the like. It will be further understood that the distal region 210 of the therapy delivery element 200 may be implanted in any suitable region where therapy delivery is desired. It will be further understood that the therapeutic agent eluting element 100 may be implanted along side the therapy delivery element 200 along the length that the delivery element 200 is tunneled subcutaneously, regardless of where the active device 1 and the distal portion 210 of the therapy delivery element 200 are implanted. While not shown, it will be understood that therapy delivery element 20 may be operably coupled to an external device (not shown), as opposed to or in addition to being operably couplable to an implantable device 1.

Figure 2:
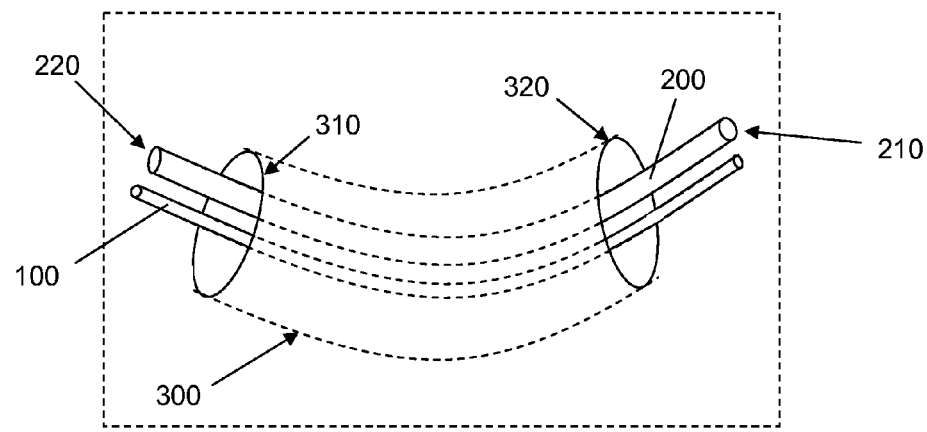
FIG. 2 is a schematic view of a therapy delivery element and a therapeutic agent eluting element implanted in a subcutaneous path.

Referring to FIG. 2, a schematic view of a therapeutic agent eluting element 100 implanted along side of a therapy delivery element 200, such as a lead or catheter, in a subcutaneous path 300 is shown. In FIG. 1, the dashed rectangular box represents a portion of the patient's skin. Dashed lines within the rectangular box represent items or areas beneath the surface of the skin. The subcutaneous path extends from a first location 310; e.g. from a first incision in the skin, to a second location 320; e.g. to a second incision in the skin. The first location 310 may be in proximity to the implant site of an active medical device. That is, the first location 310 may be in proximity to the subcutaneous pocket. The second location 320 may be closer to where the distal end 210 of the therapy delivery element 200 is implanted or is to be implanted. For example, if the distal end 210 of the delivery element 200 is implanted or is to be implanted in or adjacent to the spinal cord, the second location 320 may be in proximity to the spinal cord. The therapeutic agent eluting element 100 extends the length of the subcutaneous path 300 and lies along side of the therapy delivery element 200 in the depicted embodiment. In some embodiments, excess length of the agent eluting element may extend from the first location 310 or the second location 320. The excess length may be placed subcutaneously; e.g. coiled and placed in the subcutaneous pocket into which an active medical device is implanted, or may be removed prior to closing the openings in the skin; e.g. suturing an incision.

Some representative examples of how a therapeutic agent eluting element may be implanted subcutaneously along side of a therapy delivery element are depicted in FIGS. 3-9.

Figure 3:
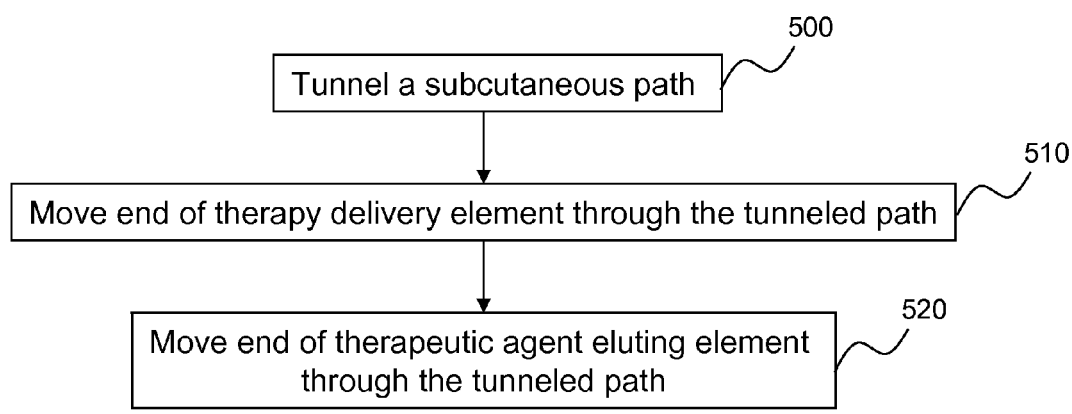
FIG. 3 is a flow diagram of a representative method for implanting a therapy delivery element and a therapeutic agent eluting element in a subcutaneous path.
Figure 4A:
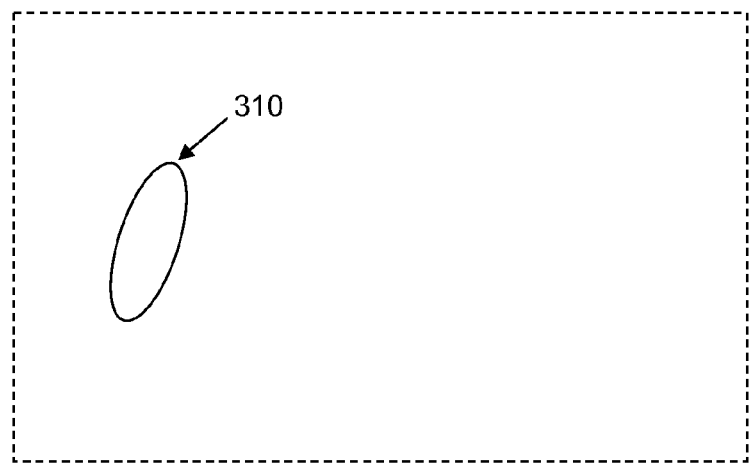
FIGS. 4A-E are schematic views of a process for creating a subcutaneous path and implanting a therapy delivery element and a therapeutic agent eluting agent in the subcutaneous path.
Figure 4B:
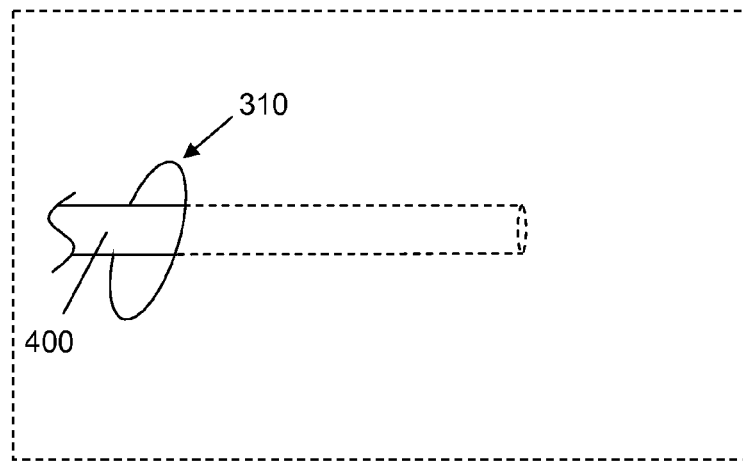
Figure 4C:
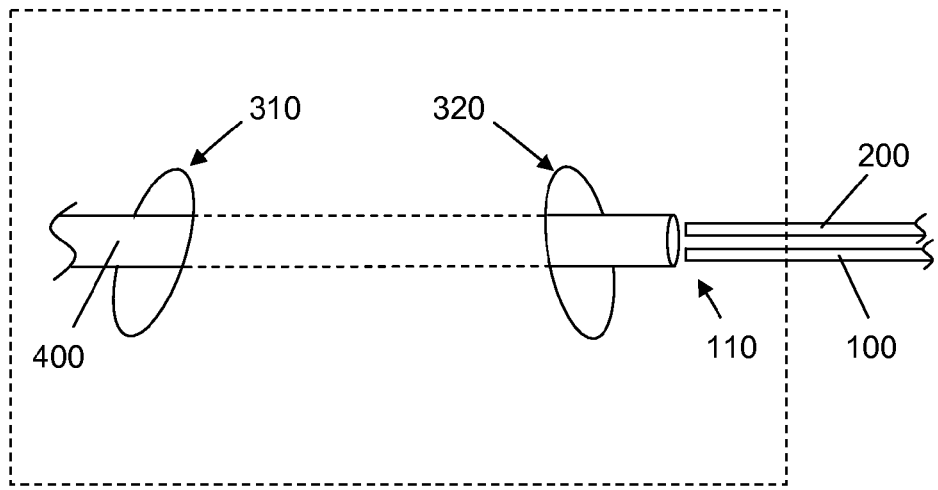
Figure 4D:
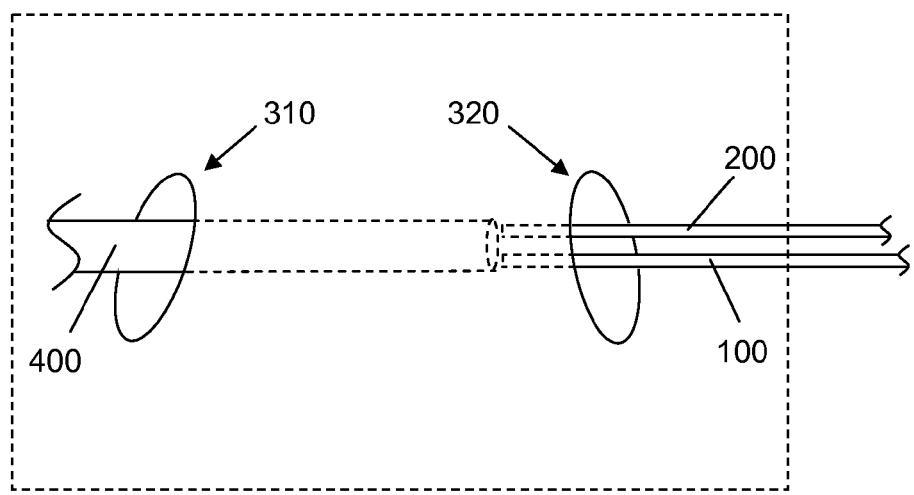

Referring now to FIG. 3, a flow diagram of a representative method is shown. The method includes tunneling a subcutaneous path in a patient (100), moving an end of a therapy delivery element through the tunneled path (110), and moving an end of a therapeutic agent eluting element through the tunneled path (120). The path may be tunneled in any suitable manner. For example, an introducer such a needle, sheath, catheter passer, dilator or the like may be tunneled subcutaneously to create a path for implanting the therapy delivery element. The implantable therapy delivery element or the therapy eluting element may be moved; e.g. pushed or pulled, through the path in any suitable manner. Some representative examples for moving the therapy delivery element and the agent eluting element through the subcutaneous pathway are described herein. However, it will be understood that other mechanisms for moving the elements through the pathway may be employed and are contemplated One example of a method for implanting a therapeutic agent eluting element along side of a therapy delivery element is depicted in FIGS. 4A-E. As shown in FIG. 4A, an incision may be made at a first skin location 310 to provide access to subcutaneous tissue. Referring to FIGS. 4B-C, an introducer 400 may be tunneled through subcutaneous tissue of a patient from the first location 310 to a second location 320. The therapy delivery element 200 and the therapeutic agent eluting element 100 may be coupled to the introducer 400 and the introducer may be withdrawn from the subcutaneous tissue to draw the elements 100, 200 through the tissue (see, FIGS. 4D-E). The therapy delivery element 200 and the agent eluting element may be coupled to the introducer 400 via any suitable mechanism. For example, the elements 100, 200 may be clamped, adhered, tied, or otherwise affixed to the introducer 400. In some embodiments, the elements 100, 200 are coupled to each other and then coupled to the introducer. For example, the agent eluting element 100 may be tied to the therapy delivery element 200, and then a compressive force; e.g. via a clamp, may be used to affix the eluting element 100 to the introducer 400 to allow the elements 100, 200 to be drawn through the tissue as the introducer 400 is withdrawn. In many circumstances, it will be desirable to subject the agent eluting element 100 to strain, stress, chemical adhesive, or the like, rather than the therapy delivery element 200, because damaging the therapy delivery element 200 may have more severe or longer lasting adverse consequences. If a portion of the agent eluting element 100 is damaged or tainted due to chemical or mechanical forces employed to move the element 100 through tissue, the damaged portion can be ignored or removed without altering the effectiveness of the element 100. By way of example if the proximal end portion 120 of the element 100 contains adhesive used to couple the element 100 to the introducer 400, the proximal end portion 110 may be cut and removed after the element 100 has been tunneled through the subcutaneous path.

Figure 4E:
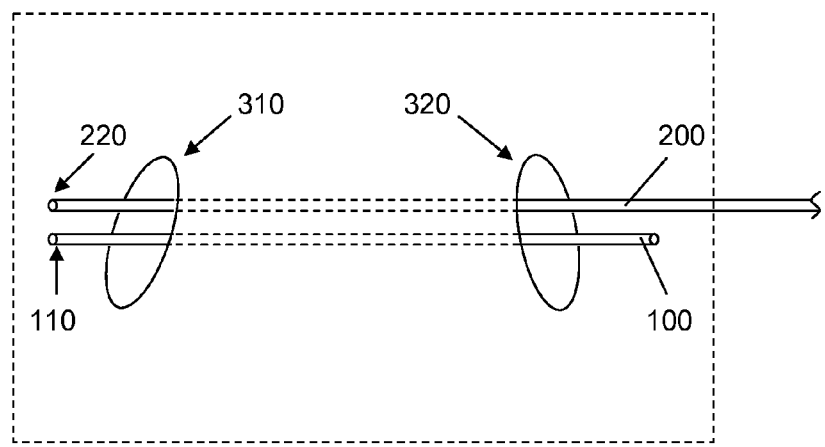

In the embodiment depicted in FIG. 4E and other depicted embodiments, the distal end of the therapy delivery element 200 is shown extending out of the patient. The distal end of the therapy delivery element 200 may be implanted in a target region of a patient following subcutaneous routing of the proximal end 220 to the first location; e.g. a subcutaneous pocket into which an active device is or is to be implanted. In many embodiments, the distal end of the delivery element 200 is positioned at a target region, e.g. epidurally or intrathecally, and the therapy delivery element 200 is anchored in proximity to the second location 320 to minimize movement of the distal end 210 once implanted. The proximal end 220 is then moved through the subcutaneous path 300 to the first location 310.

Figure 5:
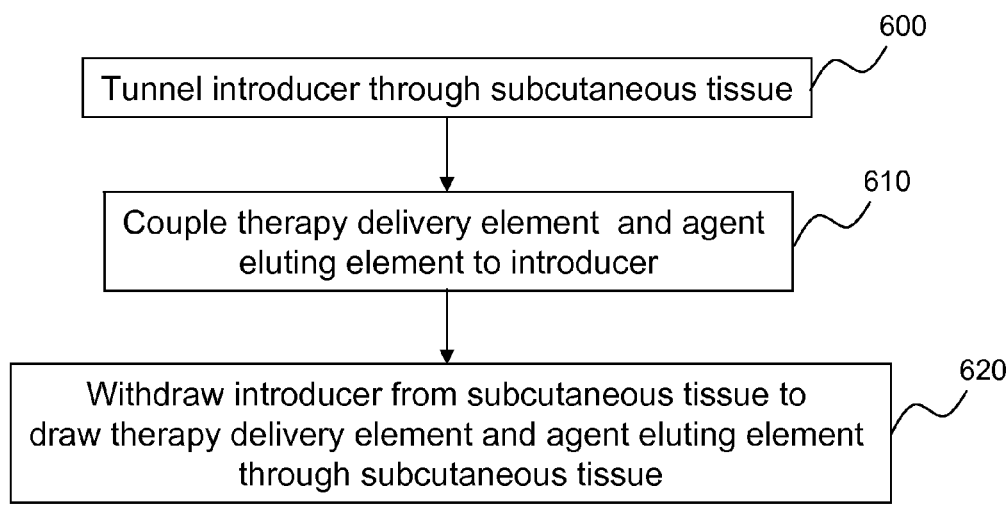
FIGS. 5-6 are flow diagrams of representative methods for implanting a therapy delivery element and a therapeutic agent eluting element in a subcutaneous path.

An overview of a representative method is illustrated in the flow diagram of FIG. 5. In the depicted method, an introducer is tunneled through subcutaneous tissue (600), the therapy delivery element and the agent eluting element are coupled to the introducer (610), and the introducer is withdrawn from the subcutaneous tissue to draw the therapy delivery element and agent eluting element through the subcutaneous tissue (620). It will be understood that if the therapy delivery element and the agent eluting element are coupled together and one of the elements are coupled to the introducer, both elements will be "coupled" to the introducer.

Figure 6:
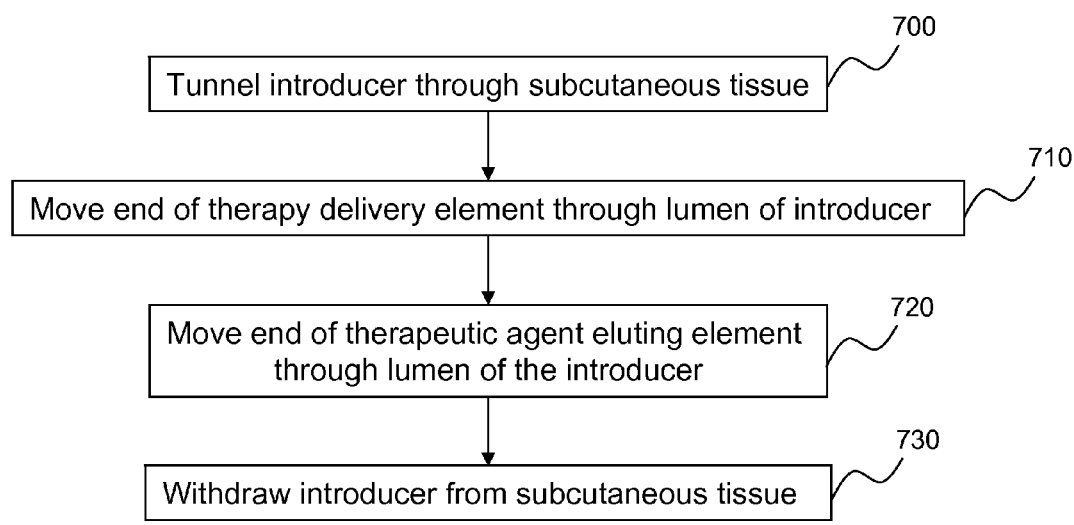

An overview of another representative method is illustrated in the flow diagram depicted in FIG. 6. In the depicted method, an introducer is tunneled through subcutaneous tissue (700). The introducer has a lumen configured to slidably receive a therapy delivery element and an agent eluting element. The method further includes moving an end of a therapy delivery element through the lumen of the introducer (710) and moving an end of a therapeutic agent eluting element through the lumen of the introducer (720). The therapy delivery element and the agent eluting element may be coupled so that moving one element through the lumen causes the other element to move through the lumen. By way of example, the proximal end region of the agent eluting element may be tied to the proximal end region of the therapy delivery element. The method further includes withdrawing the introducer from the subcutaneous tissue (730), preferably after the elements have been moved through the lumen.

Figure 7A:
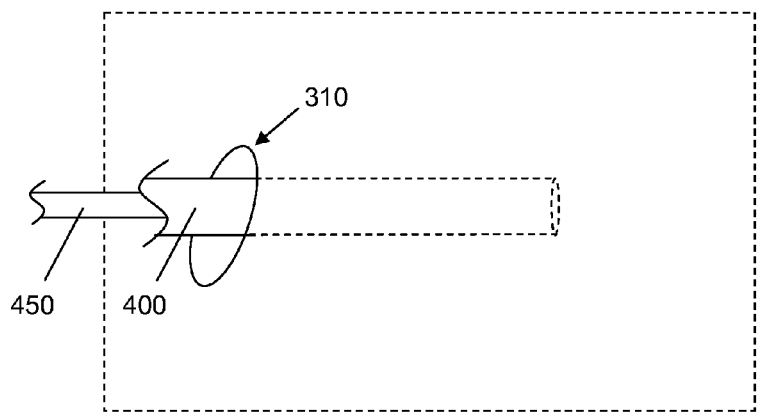
FIGS. 7A-E are schematic views of a process for creating a subcutaneous path and implanting a therapy delivery element and a therapeutic agent eluting agent in the subcutaneous path.
Figure 7B:
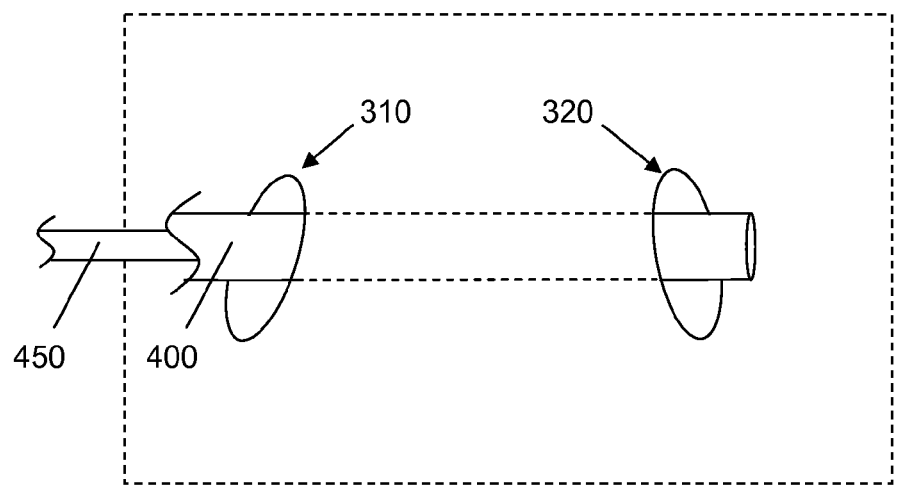
Figure 7C:
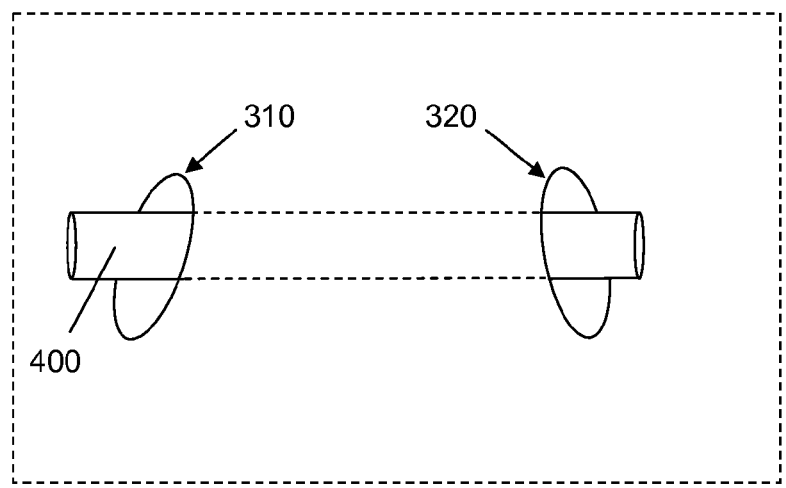
Figure 7D:
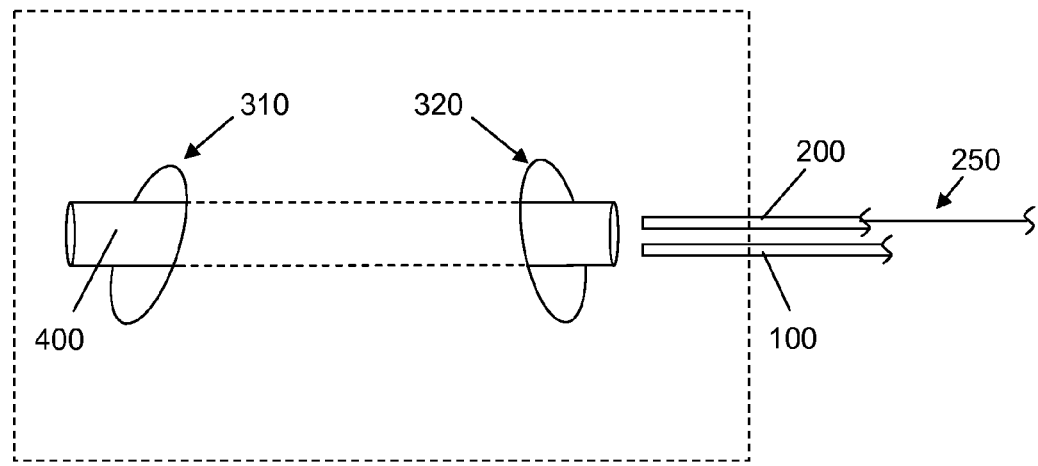
Figure 7E:
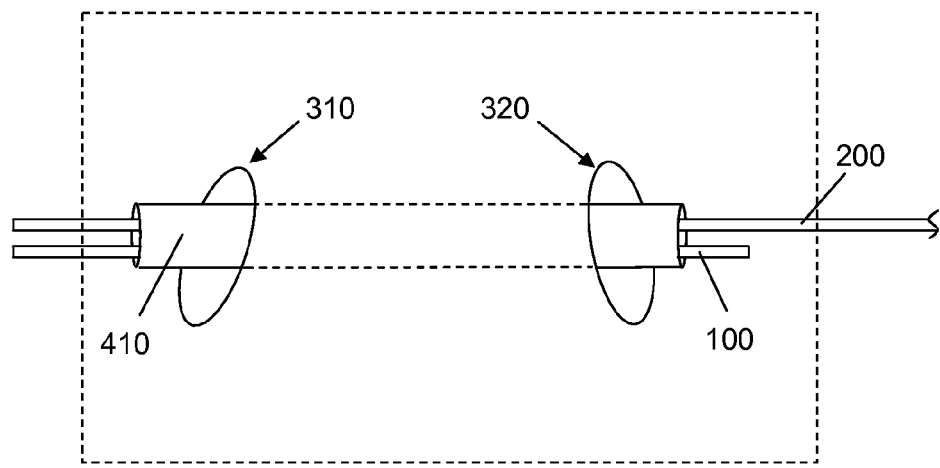

FIGS. 7A-E illustrates a schematic embodiment of the method described with regard to FIG. 6. As shown in FIGS. 7A-B, an incision or opening in a patient's skin may be made at a first location 310. An introducer 400 having a lumen may be tunneled subcutaneously from the first location 310 towards a second location 320. A stylet 450 may be inserted into the lumen of the introducer 400 to keep the lumen relatively free from tissue debris as the introducer 400 is advanced subcutaneously. Referring to FIGS. 7C, the stylet may be removed from the lumen of the introducer 400 leaving a subcutaneous conduit through which a therapy delivery element and an agent eluting element may be passed; e.g. as depicted in FIGS. 7D-E. As shown in FIG. 7D, a stylet 250 may be employed to facilitate movement of therapy delivery element 200 through the lumen of the introducer 400. Such a stylet 250 may be particularly desirable when therapy delivery element 200 has a lumen into which the stylet 250 may inserted, such as when the therapy delivery element 200 is a drug delivery catheter.

In the embodiment depicted in FIGS. 7A-E, the therapy delivery element 200 and the agent eluting element 100 are pushed through the lumen of the introducer. In some embodiments, the therapy delivery element 200 or the agent eluting element 100 are pulled through the lumen. By way of example, the therapy delivery element 200 or the agent eluting element 100 may be coupled to the stylet 450 (see FIGS. 7A-B) and pulled through the lumen of the introducer 400 when the stylet 450 is withdrawn from the lumen.

Figure 8:
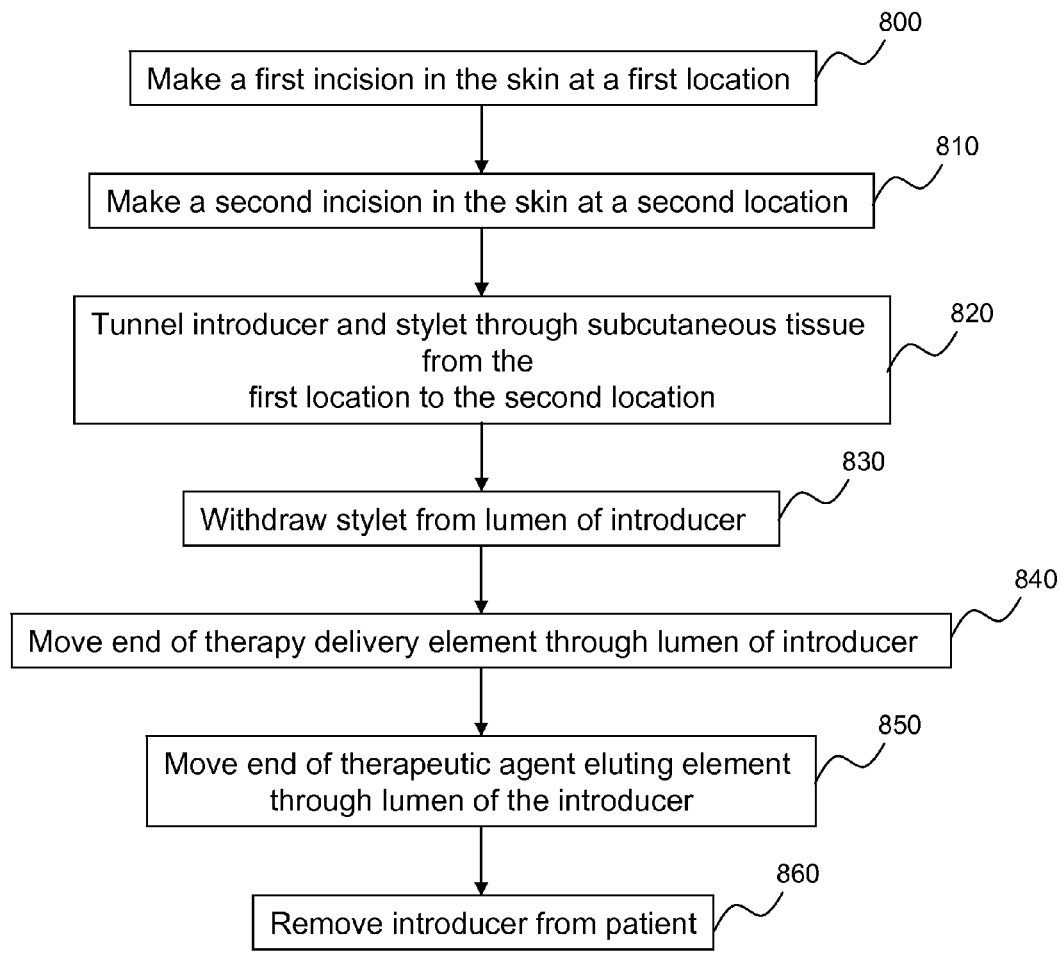
FIG. 8 is a flow diagram of a representative method for implanting a therapy delivery element and a therapeutic agent eluting element in a subcutaneous path.
Figure 9:
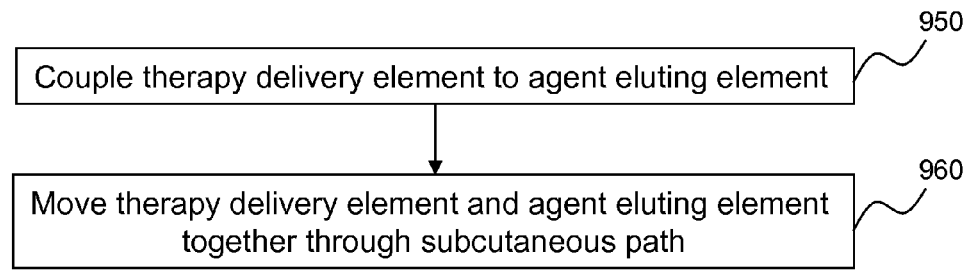
FIG. 9 is a flow diagram of representative steps for moving a therapy delivery element and a therapeutic agent eluting element together through a subcutaneous path.

FIG. 8 is a flow diagram of a representative method showing steps similar to those depicted in, and discussed with regard to, FIGS. 7A-E. The method depicted in FIG. 8 includes (i) making a first incision in the skin at a first location (800), (ii) making a second incision in the skin at a second location (810), (iii) tunneling an introducer and stylet through subcutaneous tissue from the first location to the second location (820), (iv) withdrawing the stylet from the lumen of the introducer (830), (v) moving an end of a therapy delivery element through the lumen of the introducer (840), (vi) moving an end of a therapeutic agent eluting element through the lumen of the introducer (850), and (vii) removing the introducer from the patient to leave the therapeutic agent eluting element implanted subcutaneously along side the therapy delivery element (860). As depicted in the flow diagram of FIG. 9, the therapy delivery element and the agent eluting element may be coupled (950) and moved through the lumen of the introducer together (960).

While not shown, it will be understood that the proximal or distal portions of the therapy delivery element or the therapeutic agent eluting element may be anchored to tissue in proximity to the first or second tissue location to inhibit movement or migration of the therapy delivery element or the therapeutic agent eluting element through the subcutaneous path. In some embodiments, the agent eluting element is affixed, adhered, fastened, or the like to the therapy delivery element, and the therapy delivery element or the agent eluting element is anchored to the tissue to secure both elements relative to the tissue.

Figure 10A:
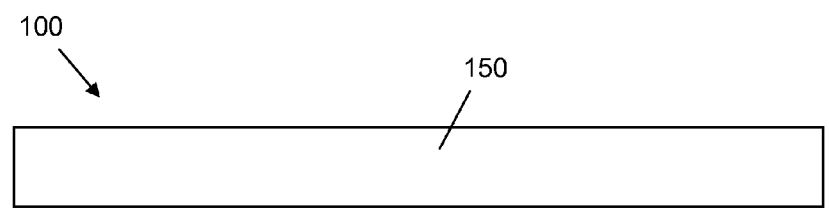
FIG. 10A is a schematic side view of a representative therapeutic agent eluting element.
Figure 10B:
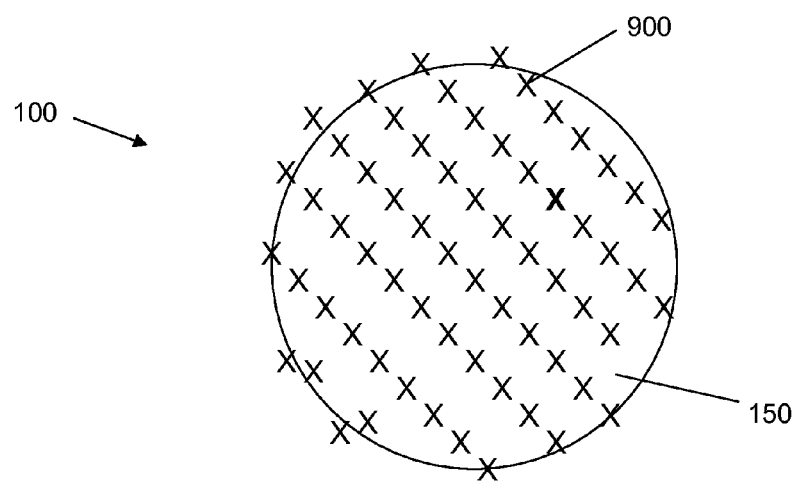
FIG. 10B is a schematic radial cross section of an embodiment of an element of FIG. 10A.

Referring now to FIGS. 10A-B, in which a schematic side (A) and radial cross sectional (B) views are shown, a therapeutic agent eluting element 100 includes an elongate body member 150 into or onto which one or more therapeutic agents 900 are incorporated. The elongate body member 150 may be formed from any suitable material with which or onto which a therapeutic agent 900 may be associated. In many embodiments, the body member 150 is formed from a polymeric material into or onto which therapeutic agent is incorporated. In some embodiments, the body member 150 is formed from a biodegradable polymeric material, such as synthetic or natural bioabsorbable polymers.

Suitable synthetic bioabsorbable polymeric materials that can be used to form the body member 150 include poly (L-lactic acid), polycaprolactone, poly(lactide-co-glycolide), poly(ethylene-vinyl acetate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly (ether-esters) such as PEO/PLA, polyalkylene oxalates, and polyphosphazenes. In various embodiments, the polymeric materials include or are formed from natural bioabsorbable polymers such as fibrin, fibrinogen, cellulose, starch, collagen, and hyaluronic acid.

The one or more therapeutic agent 900 may be associated with the body member 150 in any suitable manner. In various embodiments, at least a portion of the therapeutic agent 900 is associated with the body member 150 such that, when the element 100 is contacted with a tissue or fluid of a patient, the therapeutic agent 900 releases from the body member or elutes into the tissue or fluid. While not shown, it will be understood that the body member 150 may be formed from more than one layer, where each lay contains one or more of the same or different therapeutic agents 900. It will also be understood that the body member 150 may be tubular rather than solid as depicted in FIG. 10B.

Regardless of the material(s) from which the body 150 is formed, one or more therapeutic agents 900 are disposed in, on, or about, generally associated with, one or more layers of the body member 150 of the element 100 such that an effective amount of therapeutic agent 900 may be released from the body member 150 for a desired period of time. As used herein, "released", "eluted", or the like, as it relates to a therapeutic agent 900 released from an element 100, means being placed in a position to carry out a therapeutic effect when the element 100 is implanted in a patient. For example, the therapeutic agent 900 may elute from the body member 150 into surrounding tissue or may migrate to an external surface of the body member 150 to exert an intended effect. The element 100 or body member 150 may include therapeutic agent 900 at any suitable concentration. For example, therapeutic agent 900 may comprise about 0.1% to about 50%, or from about 1% to about 10%, of the weight of the body member 150 or a layer of a body member 150. In some circumstances, it may be desirable to place a higher concentration of therapeutic agent 900 in one or more layers relative to other layers; e.g., when continued infusion of therapeutic agent 900 into patient tissue over time is desired.

The release profile of therapeutic agent 900 from the element 100 may be varied. As described above, location of therapeutic agent 900 in or on the element 100, as well as concentration of therapeutic agent 900 at a location, provides a means for achieving control over when therapeutic agent 900 is released. The release profile may be varied by controlling the nature of the therapeutic agent 900 to be released. For example, agents 900 having greater molecular mass or size may elute more slowly than agents 900 having lesser molecular mass or size. Interactions between therapeutic agent 900 and components of body member 150 or layers of the body member 150 may also affect the rate at which therapeutic agent 900 is released from the element 100. With these and other considerations in mind, it may be desirable, in some circumstances, to vary the location of slower eluting therapeutic agents 900 and faster eluting therapeutic agents 900 within or on the element 100.

For example, in situations, e.g. where the element 100 may be permanently implanted into a subject, it may be desirable to elute roughly the same amount of a therapeutic agent 900 over a period of time. One way to achieve substantially uniform release of two or more therapeutic agents 900 over time is to dispose a slower eluting therapeutic agent 900 near surface of the element from which the agent will elute and dispose a faster eluting therapeutic agent 900 further from the surface from which the agents will elute. Alternatively, it may be desirable to load a substantial amount of reserve therapeutic agent 900, whether slow or fast eluting, into or on element 100, such that the reserve replenishes the supply of therapeutic agent 900 at or near the surface of element 100 from which the agent 900 will be released. In some situations in may be desirable to load a therapeutic agent 900 in a delayed release vector, which vector is disposed in, on or about the body member or a layer of the body member, and load different therapeutic agent 900 in the body member 150.

The rate at which therapeutic agent may be released from the therapeutic agent eluting element into tissue may also be controlled by properties of coating layers, vectors, or body members, as well as the manner in which therapeutic agent is disposed on or in coating layers or body members.

In various embodiments, one or more therapeutic agents are coated onto an underlying substrate of the body member of a therapeutic agent eluting element to form a coating layer. The coating layer may be formed of any material capable of releasing the one or more therapeutic agents into tissue when placed implanted in a patient. Preferably, the coating layer is suitable for at least temporary use within a human body. The coating layer is also preferably compatible with therapeutic agent.

Examples of commonly used materials that may be used to form coating layers include polymers such as silicones, polyamines, polystyrene, polyurethane, acrylates, polysilanes, polysulfone, methoxysilanes, and the like. Of course, any suitable polymeric material may be utilized. In some embodiments, the polymeric material of a coating is biodegradable.

Coating layers may include or be formed from polymeric materials designed to control the rate at which therapeutic agent is released from the polymeric material. Any known or developed technology may be used to control the release rate. For example, a coating layer may be designed according to the teachings of WO/04026361, entitled "Controllable Drug Releasing Gradient Coating for Medical Devices."

A coating layer or body member of the therapeutic agent eluting element may be in the form of a tube, sheath, sleeve, coating, or the like. A coating layer or body member may be extruded, molded, or the like. A coating layer may be coated on a substrate portion of a body member, grafted onto a substrate portion of a body member, embedded within a body member, adsorbed to a body member, etc. Polymers of coating layers may be porous or non-porous. Porous materials known in the art include those disclosed in U.S. Pat. No. 5,609,629 (Fearnot et al.) and U.S. Pat. No. 5,591,227 (Dinh et al.). Typically polymers are non-porous. However, non-porous polymers may be made porous through known or developed techniques, such as extruding with $CO_2$ or by foaming the polymeric material prior to extrusion or coating.

Depending upon the type of materials used to form coating layers, the coatings can be applied to the surface of a substrate portion of a body member or an underlying coating layer through any coating processes known or developed in the art. One method includes directly bonding the coating material to a surface of a substrate. By directly attaching a polymer coating to the substrate, covalent chemical bonding techniques may be utilized. The substrate surface may possess chemical functional groups on its surface such as carbonyl groups, primary amines, hydroxyl groups, or silane groups which will form strong, chemical bonds with similar groups on polymeric coating material utilized. In the absence of such chemical forming functional group, known techniques may be utilized to activate the material's surface before coupling the coating or therapeutic agent. Surface activation is a process of generating, or producing, reactive chemical functional groups using chemical or physical techniques such as, but not limited to, ionization, heating, photochemical activation, oxidizing acids, sintering, physical vapor deposition, chemical vapor deposition, and etching with strong organic solvents. Alternatively, the coating may be indirectly bound to a substrate through intermolecular attractions such as ionic or Van der Waals forces.

One or more therapeutic agents may be incorporated into a coating layer or body member in any suitable manner. For example, the therapeutic agent can be covalently grafted to a polymer of the coating layer or body member, either alone or with a surface graft polymer. Alternatively, therapeutic agent may be coated onto the surface of the polymer either alone or intermixed with an overcoating polymer. Therapeutic agent may be physically blended with a polymer of a coating layer or body member as in a solid-solid solution. Therapeutic agent may be impregnated into a polymer by swelling the polymer in a solution of the appropriate solvent. Any means of incorporating therapeutic agent into or on a coating layer or body member may be used, provided that therapeutic agent may be released, leached or diffuse from coating layer on contact with bodily fluid or tissue.

A polymer of a coating layer or body member and a therapeutic agent may be intimately mixed either by blending or using a solvent in which they are both soluble. This mixture can then be formed into the desired shape or coated onto an underlying structure of the medical device. One exemplary method includes adding one or more therapeutic agents to a solvated polymer to form a therapeutic agent/polymer solution. The therapeutic agent/polymer solution can then be applied directly to the surface of body member; for example, by either spraying or dip coating the therapeutic agent eluting element. As the solvent dries or evaporates, the therapeutic agent/polymer coating is deposited on delivery element. Furthermore, multiple applications can be used to ensure that the coating is generally uniform and a sufficient amount of therapeutic agent has been applied to the therapeutic agent eluting element.

Alternatively or in addition, an overcoating polymer, which may or may not be the same polymer that forms a substrate layer of body member or an underling coating layer, and therapeutic agent are intimately mixed, either by blending or using a solvent in which they are both soluble, and coated onto body member or underling coating layer. Any overcoating polymer may be used, as long as the polymer is able to bond (either chemically or physically) to the underlying layer. Of course, a polymer layer may be swelled with an appropriate solvent, allowing a therapeutic agent to impregnate the polymer.

In some embodiments, one or more therapeutic agents are covalently grafted onto a substrate forming the body member or a layer of the body member of the therapeutic agent eluting element. This can be done with or without a surface graft polymer. Surface grafting can be initiated by corona discharge, UV irradiation, and ionizing radiation. Alternatively, the ceric ion method, previously disclosed in U.S. Pat. No. 5,229,172 (Cahalan et al.), may be used to initiate surface grafting.

It will be understood that therapeutic agent 900, as depicted in FIG. 10B or elsewhere in this disclosure, may refer to a plurality of different therapeutic agents. Any therapeutic agent(s) may be disposed in, on, or about an agent eluting element. Because it may be desirable to treat or prevent infection, inflammation, or diseases associated with implantation of a medical device, it may be desirable to dispose one or more anti-infective agents, one or more anti-inflammatory agents, one or more other therapeutic agents, or a combination thereof in, on, or about at least a portion of a body member of an agent releasing element. In addition or alternatively, it may be desirable to deliver a local anesthetic to reduce pain associated with the implant procedure. Additional or other agents that may be disposed in, on, or about element will be readily evident to one of skill in the art. A brief summary of some non-limiting classes of therapeutic agents that may be used follows.

1. Anti-Infective Agents

Any anti-infective agent may be used in accordance with various embodiments of the invention. As used herein, "anti-infective agent" means an agent that kills or inhibits the growth of an infective organism, such as a microbe or a population of microbes. Anti-infective agents include antibiotics and antiseptics.

A. Antibiotic

Any antibiotic suitable for use in a human may be used in accordance with various embodiments disclosed herein. The antibacterial agent may have bateriostatic and/or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, which is herein incorporated by reference in its entirety, may also be used. One of ordinary skill in the art will recognize other antibiotics that may be used.

In general, it is desirable that the selected antibiotic(s) kill or inhibit the growth of one or more bacteria that are associated with infection following surgical implantation of a medical device. Such bacteria are recognized by those of ordinary skill in the art and include *Stapholcoccus aureus, Staphlococcus epidermis*, and *Escherichia coli*. Preferably, the antibiotic(s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that antimicrobial agents having different mechanisms of action and/or different spectrums of action may be most effective in achieving such an effect. In an embodiment, a combination of rifampin and micocycline is used. In an embodiment, a combination of rifampin and clindamycin is used.

B. Antiseptic

Any antiseptic suitable for use in a human may be used in accordance with various embodiments. As used herein, "antiseptic" means an agent capable of killing or inhibiting the growth of one or more of bacteria, fungi, or viruses. Antiseptic includes disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazene, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

It is desirable that the antiseptic(s) selected kill or inhibit the growth of one or more microbe that are associated with infection following surgical implantation of a medical device. Such microbes are recognized by those of ordinary skill in the art and include *Stapholcoccus aureus, Staphococcus epidermis, Escherichia coli, Pseudomonus aruginosa,* and *Candidia.*

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action and/or different spectrums of action may be most effective in achieving such an effect. In a particular embodiment, a combination of chlorohexidine and silver sulfadiazine is used.

C. Antiviral

Any antiviral agent suitable for use in a human may be used in accordance with various embodiments. Nonlimiting examples of antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. One of ordinary skill in the art will recognize other antiviral agent that may be employed in accordance with this disclosure.

To enhance the likelihood that viruses will be killed or inhibited, it may be desirable to combine two or more antiviral agents. It may also be desirable to combine one or more antiseptics with one or more antiviral agent.

D. Anti-Fungal

Any anti-fungal agent suitable for use in a human may be used in accordance with various embodiments. Nonlimiting examples of anti-fungal agents include amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione. One of ordinary skill in the art will recognize other anti-fungal agents that may be employed in accordance with this disclosure.

To enhance the likelihood that fungi will be killed or inhibited, it may be desirable to combine two or more anti-fungal agents. It may also be desirable to combine one or more antiseptics with one or more anti-fungal agent.

E. Elution Profile and Concentration of Anti-Infective Agents

As discussed in more detail in co-pending application Ser. No. 12/104,932, filed on Apr. 17, 2008 and published on Oct. 23, 2008 as US 2008/0260796, anti-microbial agents can be effective at preventing infection when rapidly eluted from a polymeric material placed in proximity to an implantable medical device. Accordingly, in some embodiments where one or more antimicrobial agents are associated with a therapeutic agent eluting element as described herein, 60% or more (e.g., 70% or more, 80% or more, etc.) of anti-infective agent associated with the article to elute within 24 hours of being implanted in a patient. In some embodiments, substantially all the antimicrobial agent is eluted within 72 hours. In some embodiments, substantially all the antimicrobial agent is eluted within 24 hours. In various embodiments, a therapeutic agent eluting element is configured to elute 40% or more of anti-infective agent associated with the therapeutic agent eluting element within 48 hours of being implanted in a patient. In some embodiments, substantially all the antimicrobial agent is eluted within one week.

As further discussed in co-pending application Ser. No. 12/104,932, filed on Apr. 17, 2008 and published on Oct. 23, 2008 as US 2008/0260796, anti-microbial agents can be effective at preventing infection when they are included in articles having relatively small surface areas relative to the surface area of the primary implantable medical device. Accordingly, in some embodiments where one or more antimicrobial agents are associated with a therapeutic agent eluting element as described herein, the exterior surface area of the therapeutic agent eluting element is 30% or less, 20% or less, 10% or less, or 5% or less than the external surface area of device. As used herein, "surface area" is calculated on a macroscopic scale. For example, a smooth surface will be considered to have the same surface area as a rough or porous surface.

As further discussed in co-pending application Ser. No. 12/104,932, filed on Apr. 17, 2008 and published on Oct. 23, 2008 as US 2008/0260796, anti-microbial agents can be effective at preventing infection even at low concentrations. Accordingly, in some embodiments where one or more antimicrobial agents are associated with a therapeutic agent eluting element as described herein, an anti-infective agent comprises 0.1% to 50%, 0.1% to 20%, 0.1% to 5%, 1% to 10%, etc. of the weight of the therapeutic agent eluting element. In various embodiments, one or more anti-infective agent may be present in the article in an amount of 0.25 to 1% by weight of the article. In various embodiments, a therapeutic agent eluting element includes between about 100-2000 micrograms of rifampin and between about 100-2000 micrograms of minocycline.

In various embodiments, at least 200 micrograms of minocycline and rifampin are capable of being eluted from the therapeutic agent eluting element in a 24 hour time period between six and seven days, between five and six days, between four and five days, between three and four days, between two and three days, between one and two days, or within one day following implantation. Alternatively, or in addition, the therapeutic agent eluting element may contain 300 micrograms or less of minocycline or rifampin seven, six, five, four, three, two, or one day following implantation.

In some embodiments, a therapeutic agent eluting element contains between 1 and 500 micrograms (e.g., between 1 and 100 micrograms, between 3 and 50 micrograms or between 5 and 25 micrograms) of minocycline per square inch of the external surface area of the active implantable medical device and between 1 and 500 micrograms (e.g., between 1 and 100 micrograms, between 3 and 50 micrograms or between 5 and 25 micrograms) of rifampin per square inch of the external surface area of the active implantable medical device. In numerous embodiments where the therapeutic agent eluting element includes an anti-infective agent other than minocycline or rifampin, the amount of the anti-infective agent associated with the therapeutic agent eluting element is determined as follows: Multiply minimum inhibitory concentration (MIC) of the anti-infective agent against a strain of S. aureus in an amount per milliliter by the product of one milliliter times a number between the range of 1,500 and 50,000; i.e., (MIC) times (1 ml) times (between 1,500 and 50,000).

2. Anti-Inflammatory Agents

Any anti-inflammatory agent suitable for use in a human may be used in accordance with various embodiments. Non-limiting examples of anti-inflammatory agents include steroids, such as cortisone, hydrocortisone, prednisone, dexamethasone, methyl-prednisilone, an derivatives thereof; and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

3. Local Anesthetics

Any local anesthetic agent suitable for use in a human may be used in accordance with various embodiments. Non-limiting examples of local anesthetics agents include lidocaine, prilocaine, mepivicaine, benzocaine, bupivicaine, amethocaine, lignocaine, cocaine, cinchocaine, dibucaine, etidocaine, procaine, veratridine (selective c-fiber blocker) and articaine.

Any other suitable therapeutic agent or combination of therapeutic agents may be included in a therapeutic agent eluting element as described or contemplated herein.

Thus, embodiments of the ELEMENT FOR IMPLANTATION WITH MEDICAL DEVICE are disclosed. One skilled in the art will appreciate that the present invention can be practiced with embodiments other than those disclosed. The disclosed embodiments are presented for purposes of illustration and not limitation.

What is claimed is:

1. A therapeutic agent eluting element consisting essentially of:
   an elongate body member; and
   one or more therapeutic agents incorporated into or onto the body member, wherein the one or more therapeutic agents are elutable from the body member when the body member is contacted with tissue or fluid of a patient,
   wherein the elongate body member is formed from a polymeric material, and wherein the element is configured to be implanted subcutaneously along side of a therapy delivery element, wherein the therapy delivery element is selected from the group consisting of a catheter and a lead, and
   wherein the elongate body member is solid and lumen free.

2. The element of claim 1, wherein the body member consists essentially of a biodegradable polymeric material.

3. The element of claim 1, wherein the one or more therapeutic agents are selected from the group consisting of an anti-infective agent, an anti-inflammatory agent, and a local anesthetic.

4. The element of claim 1, wherein the one or more therapeutic agent comprises minocycline and rifampin.

5. A system comprising:
   an introducer configured to tunnel a subcutaneous path in a patient;
   an implantable therapy delivery element configured to be at least partially implanted in a subcutaneous tissue of a patient, wherein the therapy delivery element is selected from the group consisting of a catheter and a lead; and
   a therapeutic agent eluting element configured to be implanted along side of the therapy delivery element in the subcutaneous tissue, wherein the therapeutic agent eluting element comprises an elongate body member formed from a polymeric material and one or more therapeutic agents elutable from the body member, wherein the body member is solid and lumen free.

6. The system of claim 5, wherein the therapy delivery element is a catheter configured to be operably coupled to an infusion device.

7. The system of claim 5, wherein the therapeutic agent eluting element and the introducer are configured such that therapeutic agent eluting element is coupleable to the introducer while the introducer is advanced through subcutaneous tissue.

8. The system of claim 5, wherein the body member of the therapeutic agent eluting element consists essentially of a bio-degradable polymeric material.

9. The system of claim 5, wherein the one or more therapeutic agents are selected from the group consisting of an anti-infective agent, an anti-inflammatory agent, and a local anesthetic.

10. The system of claim 5, wherein the one or more therapeutic agent comprises minocycline and rifampin.

* * * * *